(12) United States Patent
Yamaoka et al.

(10) Patent No.: US 7,341,846 B2
(45) Date of Patent: Mar. 11, 2008

(54) METHOD OF MEASURING GLUCOSE CONCENTRATION AND GLUCOSE SENSOR WITH THE USE OF GLUCOSE DEHYDROGENASE

(75) Inventors: Hideaki Yamaoka, Kyoto (JP); Mitsuhiro Hoshijima, Kyoto (JP); Tomomichi Tsujimoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 0 days.

(21) Appl. No.: 10/518,858

(22) PCT Filed: Jun. 16, 2003

(86) PCT No.: PCT/JP03/07630

§ 371 (c)(1),
(2), (4) Date: Aug. 11, 2005

(87) PCT Pub. No.: WO03/106702

PCT Pub. Date: Dec. 24, 2003

(65) Prior Publication Data

US 2006/0035300 A1 Feb. 16, 2006

(30) Foreign Application Priority Data

Jun. 17, 2002 (JP) ............................. 2002-176368

(51) Int. Cl.
*C12Q 1/32* (2006.01)
(52) U.S. Cl. ...................................................... 435/26
(58) Field of Classification Search ..................... None
See application file for complete search history.

(56) References Cited

U.S. PATENT DOCUMENTS 4,840,893 A 6/1989 Hill et al.
6,212,417 B1 4/2001 Ikeda et al.

FOREIGN PATENT DOCUMENTS

| EP | 1 331 272 | 7/2003 |
| EP | 1 426 757 | 6/2004 |
| JP | 11/507536 | 7/1999 |
| JP | 2000-65778 | 3/2000 |
| WO | 96/39534 | 12/1996 |
| WO | 02/36779 | 5/2002 |
| WO | WO 02/36779 | 5/2002 |

OTHER PUBLICATIONS

Hawthorne et al. Biochem J. 1939;33(10):1573-1579.*
Yum et al. J Bacteriol. 1997;179(21)6566-6572.*
Chen et al. Anal. Chem. 2001;73:2862-2868.*
European Search Report, mailed May 30, 2006 for Application No. EP 03 73 3454.
Reiter et al., "Redox Modification of Proteins Using Sequential-Parallel Electrochemistry in Microtiter Plates", *Analyst*, 2001, vol. 126, pp. 1912-1918.
Morris et al., "An Electrochemical Capillary Fill Device for the Analysis of Glucose Incorporating Glucose Oxidase and Ruthenium (III) Hexamine as Mediator", *Electroanalysis*, 1992, vol. 4, pp. 1-9.
Martin et al., "Glucose Quantitation using and Immobilized Glucose Dehydrogenase Enzyme Reactor and a Tris (2,2'-bipyridyl) Ruthenium (II) Chemiluminescent Sensor," *Analytica Chimica Acta*, 1993, vol. 281, pp. 475-481.
Tolosa et al., "Glucose Sensor for Low-Cost Lifetime-Based Sensing Using a Genetically Engineered Protein", Analytical Biochemistry 267, pp. 114-120 (1999).
Cui et al., "Disposable amperometric glucose sensor electrose with enzyme-immobilized nitrocellulose strip", Talanta 54 (2001) 1105-1111.
Martin et al., Glucose quantitation using an immobilized glucose dehydrogenase enzyme reactor and a tris(2,2'-bipyridyl) ruthenium(II) chemiluminescent sensor, Analytica Chimica Acta, 281 (1993) 475-481.
Okuda et al, "The Application of Cytochromes As The Interface Molecule To Facilitate The Electron Transfer For PQQ Glucose Dehydrogenase Employing Mediator Type Glucose Sensor", Chemical & Bio-Sensors, Analytical Letters vol. 35, No. 9, pp. 1465-1478, 2002.
Yamazaki et al., "Subunit Analyses of a Novel Thermostable Glucose Dehydrogenase Showing Different Temperature Properties According to its Quaternary Structure", Applied Biochemistry and Biotechnology, vol. 77-79 (1999) pp. 325-335.

* cited by examiner

*Primary Examiner*—Ralph Gitomer
*Assistant Examiner*—Bin Shen
(74) *Attorney, Agent, or Firm*—Hamre, Schumann, Mueller & Larson, P.C.

(57) ABSTRACT

The present invention relates to a technique for measuring a glucose level by utilizing a reaction system containing an enzyme and an electron carrier. In accordance with the glucose level measuring method of the present invention, glucose dehydrogenase with cytochrome C attached thereto or glucose dehydrogenase derived from a microorganism belonging to a *burkholderia* genus is used as the enzyme, and a Ru compound is used as the electron carrier. The present invention further provides a glucose sensor in which glucose dehydrogenase with cytochrome C attached thereto or glucose dehydrogenase derived from derived from a microorganism belonging to a *burkholderia* genus is used as the enzyme, and a Ru compound is used as the electron carrier.

5 Claims, 8 Drawing Sheets

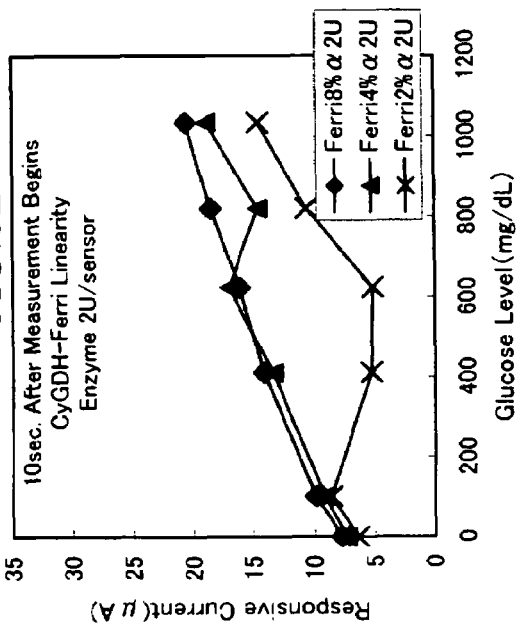
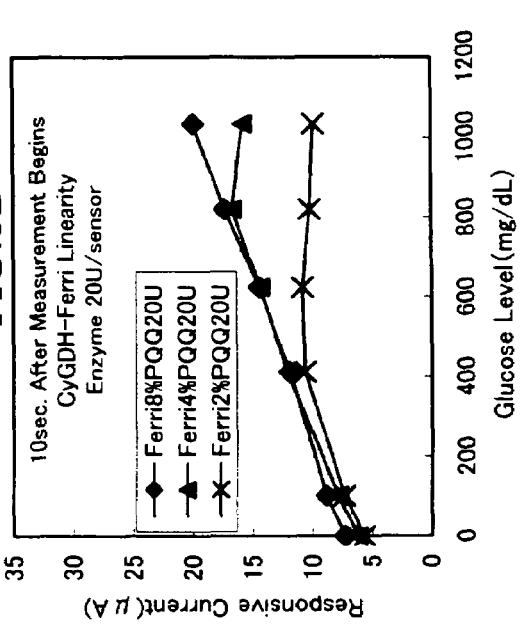
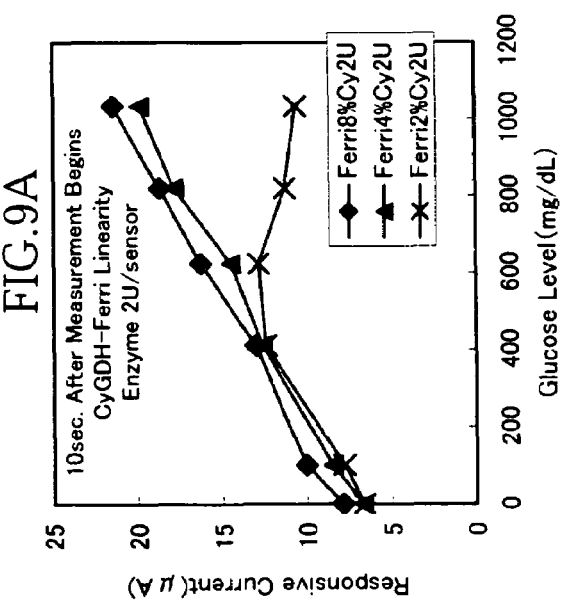
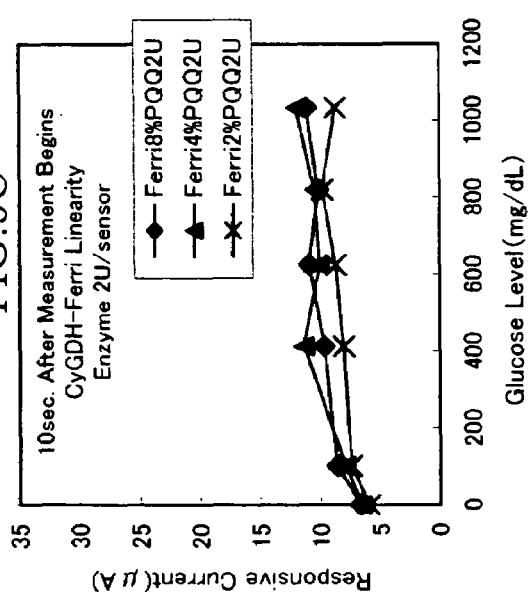

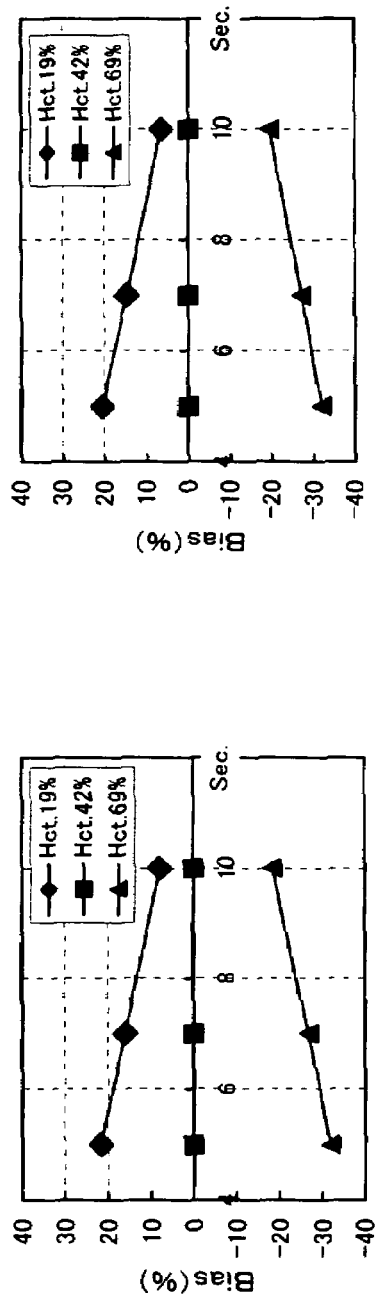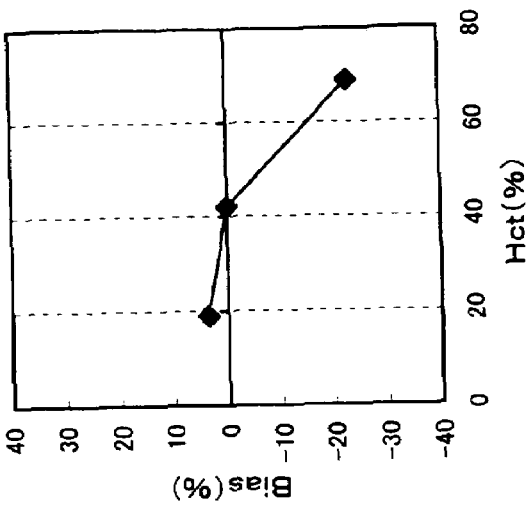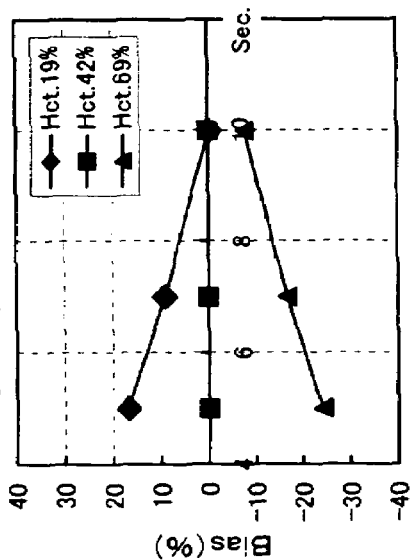

METHOD OF MEASURING GLUCOSE CONCENTRATION AND GLUCOSE SENSOR WITH THE USE OF GLUCOSE DEHYDROGENASE

TECHNICAL FIELD

The present invention relates to a technique for measuring the glucose level of a sample liquid (e.g. a biochemical sample such as blood or the modified liquid thereof).

BACKGROUND ART

It is important for diabetics to regularly check their blood glucose level for controlling the blood glucose level. However, it is troublesome to frequently visit a medical institution for measuring blood glucose level. In light of this, portable handheld blood glucose level measuring apparatuses are used, whereby diabetics can easily and conveniently measure the blood glucose level even when they are away from home, for example.

In using such a portable blood glucose level measuring apparatus, a glucose sensor for providing an enzyme reaction system is mounted to the blood glucose level measuring apparatus, and blood (analyte) is supplied to the glucose sensor for measuring the blood glucose level. Generally, in this case, the skin of the measurer is cut to extract blood, and the blood is supplied to the glucose sensor as the sample liquid. In this method, to lessen the burden on the measurer caused by the blood extraction, it is preferable that the amount of blood to be extracted is small. Therefore, various improvements have been made to enable the blood glucose level measurement by using a relatively small amount of blood (analyte).

For example, the glucose sensor comprises a substrate on which electrodes and a reagent layer are formed, and a capillary formed to accommodate the reagent layer (See FIGS. 2 and 3). The reagent layer includes oxidoreductase and an electron carrier. Generally, GOD or PQQGDH is used as the oxidoreductase, whereas potassium ferricyanide is used as the electron carrier (See JP-A 2000-65778, for example). In the glucose sensor, when the analyte is supplied to the reagent layer by using the capillary, a reaction system in a liquid phase is established in the capillary. Thus, by the oxidoreductase, oxidation reaction of e.g. glucose is catalyzed, while reduction reaction of the electron carrier is catalyzed.

In the portable blood glucose level measuring apparatus, a voltage is applied to the reaction system by using the electrodes of the glucose sensor, and the responsive current is measured. The responsive current depends on the amount of e.g. electron carrier in the reduced form (which relates to the glucose level), and utilized as the basis for computing the glucose level. The glucose level is computed by coulometry or amperometry. Coulometry is a technique in which most part of glucose in the analyte is subjected to reaction for obtaining the integrated value so that the glucose level is computed based on the integrated value (total electricity). Amperometry is a technique in which the responsive current is measured after a certain time period has elapsed from the start of the reaction so that the glucose level is computed based on the responsive current.

The reaction rate of GOD with glucose is low (Km (Michaelis constant) is high). Therefore, when coulometry is utilized in which most part of glucose in the analyte is subjected to reaction for obtaining the total electricity for computation, the measurement time becomes considerably long. Therefore, amperometry is utilized to measure the glucose level in a short period of time by using GOD as oxidoreductase.

In amperometry, however, when the glucose level is low, the enzyme reaction maybe almost completed before the responsive current is measured. In such a case, a low responsive current is measured, so that the measurement accuracy in a low concentration range is deteriorated. Further, the similar problem may occur when the amount of the analyte is considerably small, because the absolute amount of glucose is small. Such a problem may be solved by reducing the amount of enzyme to be used. However, when the amount of enzyme is small, the reaction rate of glucose is decreased. Therefore, for the analytes whose glucose levels are higher than a certain level, the difference in glucose level does not appear significantly as the difference in responsive current. As a result, when the amount of enzyme is reduced, the resolving power in the high concentration range is reduced, because the difference in glucose level cannot appear as the difference in responsive current. Therefore, amperometry is not suitable for the measurement for a small measurement range by the use of a small amount of analyte.

Moreover, the reactivity of GOD with the electron carrier is not so high. Therefore, to shorten the measurement time, a large amount of electron carrier need be used. As a result, the size reduction of the glucose sensor (reagent and capillary, to be exact) is difficult, so that the amount of analyte necessary for the measurement increases. Also from this point, the use of GOD is not suitable for the measurement of a small amount of analyte.

Under the above-described circumstances, it is said that accurate glucose level measurement by amperometry using GOD is possible only when the amount of analyte is no less than 0.6 μL which is converted to the measurement time of no less than 15 seconds and when the glucose level lies in the measurement range of 10 to 600 mg/dL.

It is known that, by coulometry using PQQGDH as oxidoreductase, the measurement of the blood glucose level is possible even with a minute amount, e.g. 0.3 μL of analyte. However, since coulometry is a technique in which most part of glucose in the analyte is used to compute the glucose level as noted above, the measurement time in a high glucose concentration range tends to become long as compared with amperometry. For example, to assure the practically necessary minimum measurement range (10-600 mg/dL), the measurement time of at least 15 to 30 seconds need be taken.

To shorten the measurement time, it may be one way to increase the content of enzyme and electron carrier in the reagent. In this case, however, the solubility of the reagent layer is reduced. Therefore, when the analyte is supplied to the capillary, it is difficult to form a reaction system in a uniform liquid phase in the capillary. As a result, due to the variation in the degree of dissolution among glucose sensors (or among measurements), the reproducibility is deteriorated or the influence of blood cell components in the blood increases, whereby the measurement accuracy is deteriorated. Particularly, since potassium ferricyanide has a low solubility to blood, the use of potassium ferricyanide as the electron carrier considerably deteriorates the measurement accuracy. Moreover, potassium ferricyanide has a low storage stability and is easily transferred to a reduced form. Therefore, an increase in the content of potassium ferricyanide leads to an increase in the background, whereby the measurement accuracy in a low glucose concentration range is deteriorated.

DISCLOSURE OF THE INVENTION

An object of the present invention is to enable accurate measurement of a small amount of analyte in a short period of time while covering a wide measurement range.

According to a first aspect of the present invention, there is provided a glucose level measuring method using glucose dehydrogenase for measuring a glucose level by utilizing a reaction system containing an enzyme and an electron carrier. According to the method, glucose dehydrogenase to which cytochrome C is attached is used as the enzyme, and a Ru compound is used as the electron carrier.

Preferably, as the cytochrome C, use may be made of one derived from a microorganism belonging to a *burkholderia* genus. As the cytochrome C, use may be made of one having a molecular weight of about 43 kDa in SDS-polyacrylamide gel electrophoresis under a reduced condition.

According to a second aspect of the present invention, there is provided a glucose level measuring method using glucose dehydrogenase for measuring glucose level by utilizing a reaction system containing an enzyme and an electron carrier. According to the method, glucose dehydrogenase derived from a microorganism belonging to a *burkholderia* genus is used as the enzyme, a Ru compound is used as the electron carrier.

In the glucose level measuring method according to the present invention, the glucose level measurement comprises providing the reaction system with stimulation, detecting response to the stimulation, and computing the glucose level based on the detected level of the response. In this case, the stimulation may be provided as voltage, whereas the response may obtained as electric current or optical characteristics, for example.

According to a third aspect of the present invention, there is provided a glucose sensor comprising a first and a second electrodes, and a reagent layer containing an enzyme and an electron carrier. The reagent layer is supplied with glucose solution to establish a reaction system which is stimulated by the first and the second electrodes. The enzyme comprises glucose dehydrogenase to which cytochrome C is attached. The electron carrier comprises a Ru compound.

Preferably, as the cytochrome C, use may be made of one derived from a microorganism belonging to a *burkholderia* genus. As the cytochrome C, use may be made of one having a molecular weight of about 43 kDa in SDS-polyacrylamide gel electrophoresis under a reduced condition.

According to a fourth aspect of the present invention, there is provided a glucose sensor comprising a first and a second electrodes, and a reagent layer containing an enzyme and an electron carrier. The reagent layer is supplied with glucose solution to establish a reaction system which is stimulated by the first and the second electrodes. The enzyme comprises glucose dehydrogenase derived from a microorganism belonging to a *burkholderia* genus. The electron carrier comprises a Ru compound.

In the present invention, as the glucose dehydrogenase, use may be made of one that includes an α subunit having a glucose dehydrogenase activity and a molecular weight of about 60 kDa in SDS-polyacrylamide gel electrophoresis under a reduced condition. The glucose dehydrogenase may be one that includes a γ subunit having a molecular weight of about 14 kDa in SDS-polyacrylamide gel electrophoresis under a reduced condition.

In the present invention, as the Ru compound, use may be made of one represented by a chemical formula as follows:

$[Ru(NH_3)_5X]^{n+}$ where X represents $NH_3$, halogen ion, CN, pyridine, nicotinamide or $H_2O$. Among these, it is preferable that X in the Ru complex is $NH_3$ or halogen ion. The n+ in the above chemical formula represents the valency of the Ru complex, which is determined by the kind of X.

Since the Ru complex is unstable in the reduced form (II), it generally exists in the oxidized form (III). Therefore, even when the Ru complex in the oxidized form is contained in the reagent layer of the glucose sensor and exposed to light or water, it is not easily reduced. Further, the Ru complex is unlikely to be crystallized and capable of keeping the state of minute particles. From this point, the Ru complex has a high solubility. Therefore, in view of the resistance to exposure and the storage stability, it is preferable that the reagent layer contains the Ru complex in the oxidized form.

For example, the glucose sensor according to the present invention may further comprise liquid retaining space in which the reagent layer is provided and sample liquid is retained. In this case, the reagent layer comprises a solid layer, and the oxidoreductase and the electron carrier dissolve at least partially in the sample liquid when the sample liquid is retained in the liquid retaining space. It is preferable that, in the glucose sensor after the sample supply, a reaction system is established as a liquid phase in the liquid retaining space by the glucose, oxidoreductase and the electron carrier.

For example, the volume of the sample retaining space is set to 0.1 to 0.5 μL for enabling measurement of a small amount of sample liquid. In this case, the content of the enzyme in the reagent layer is set to an amount corresponding to a glucose dehydrogenase activity of 1.0 to 10.0 U. One unit (U) of enzyme is defined as the amount (molar absorptivity: 4.76×1000 μM/cm) for oxidizing 1 μM of glucose every one minute when discoloration with time due to the reduction of DCIP (2, 6-dichlorophenolindophenol) is measured at 600 nm, which is an absorption wavelength of DCIP, under standard test conditions (pH6.0, 37° C.). The content of the electron carrier in the reagent layer is set so that the electron carrier has a concentration of 1.0 to 5.0 wt % when the liquid retaining space is filled with the sample liquid.

The liquid retaining space may be constructed to move the sample liquid by capillary action.

As the microorganism belonging to the *burkholderia* genus in the present invention, any microorganism may be used as long as it can produce an enzyme (hereinafter, sometimes simply referred to as "GDH") containing an α subunit having a glucose dehydrogenase activity or cytochrome C (β subunit). However, among such microorganisms, *burkholderia* cepacia, particularly *burkholderia* cepacia strain KS1 (hereinafter, sometimes simply referred to as "strain KS1") is preferable. The strain KS1, which is a novel strain separated from the soil near a hot spring, is identified as *burkholderia* cepacia from its mycological characteristics. On Sep. 25, 2000, the strain KS1 was deposited to International Patent Organism Depositary of National Institute of Advanced Industrial Science and Technology (Tsukuba Central 6, 1-1-1 Higashi, Tsukuba, Ibaraki 305-8566 Japan) as microorganism accession number FERM BP-7306. The strain KS1 can produce GDH containing an a subunit (molecular weight: about 60 kDa), a β subunit (corresponding to cytochrome C) (molecular weight: about 43 kDa), and a γ subunit (molecular weight: about 14 kDa). It is to be noted that the molecular weight is measured in SDS-polyacrylamide gel electrophoresis under the reduced condition.

Cytochrome C (including the β subunit) is electron carrying protein. From the viewpoint of improving the electron carriage speed, it is preferable to use cytochrome C as GDH in which cytochrome C is attached to a subunit (including the α subunit) having a glucose dehydrogenase activity. (Hereinafter, this GDH is sometimes simply referred to as "CyGDH"). Cytochrome C is not limited to one (β subunit) derived from a microorganism belonging to the *burkholderia* cepacia genus. For example, cytochrome C derived from other microorganisms or living cells may be used as long as it can be combined to a subunit having a glucose dehydrogenase activity and perform the electron carrying function.

As noted above, the α subunit is a subunit having a glucose dehydrogenase activity. The GDH consisting of an α subunit and a γ subunit (hereinafter, sometimes simply referred to as "αGDH") is higher, in reaction rate with glucose (Vmax/Km), than the GDH which does not contain a γ subunit. This point has been confirmed by the inventors of the present invention. Therefore, when α subunit is to be used, it is preferable to use the α subunit as GDH in which a γ subunit is attached to the α subunit from the viewpoint of increasing the reaction rate with glucose.

In the claims of the present invention, the α subunit, the cytochrome C (β subunit) or the γ subunit are specified by the original fungus, but this is merely an expedient way to specify the subunits. A vector including the expression code of the aimed subunit may be transferred to a host and this host produces GDH. There may be a case where the produced GDH is used as the glucose dehydrogenase, and the difference lies only in the origin of the GDH (subunit). As readily seen, it should be appreciated that such a case is to be included in the scope of the present invention.

BRIEF DESCRIPTION OF THE DRAWINGS

FIGS. 9A-9D each is a graph showing the relationship between the glucose level and the responsive current after ten seconds from the start of the reaction when the reagent layer is provided by using an iron complex.

FIGS. 10A-10D each is a graph evaluating the influence of hematocrit (Hct) as the Bias (with respect to the reference of Hct 42%) after the lapse of a predetermined time from the start of the reaction.

BEST MODE FOR CARRYING OUT THE INVENTION

Preferred embodiments of the present invention will be described below in detail with reference to the accompanying drawings.

Figure 1:
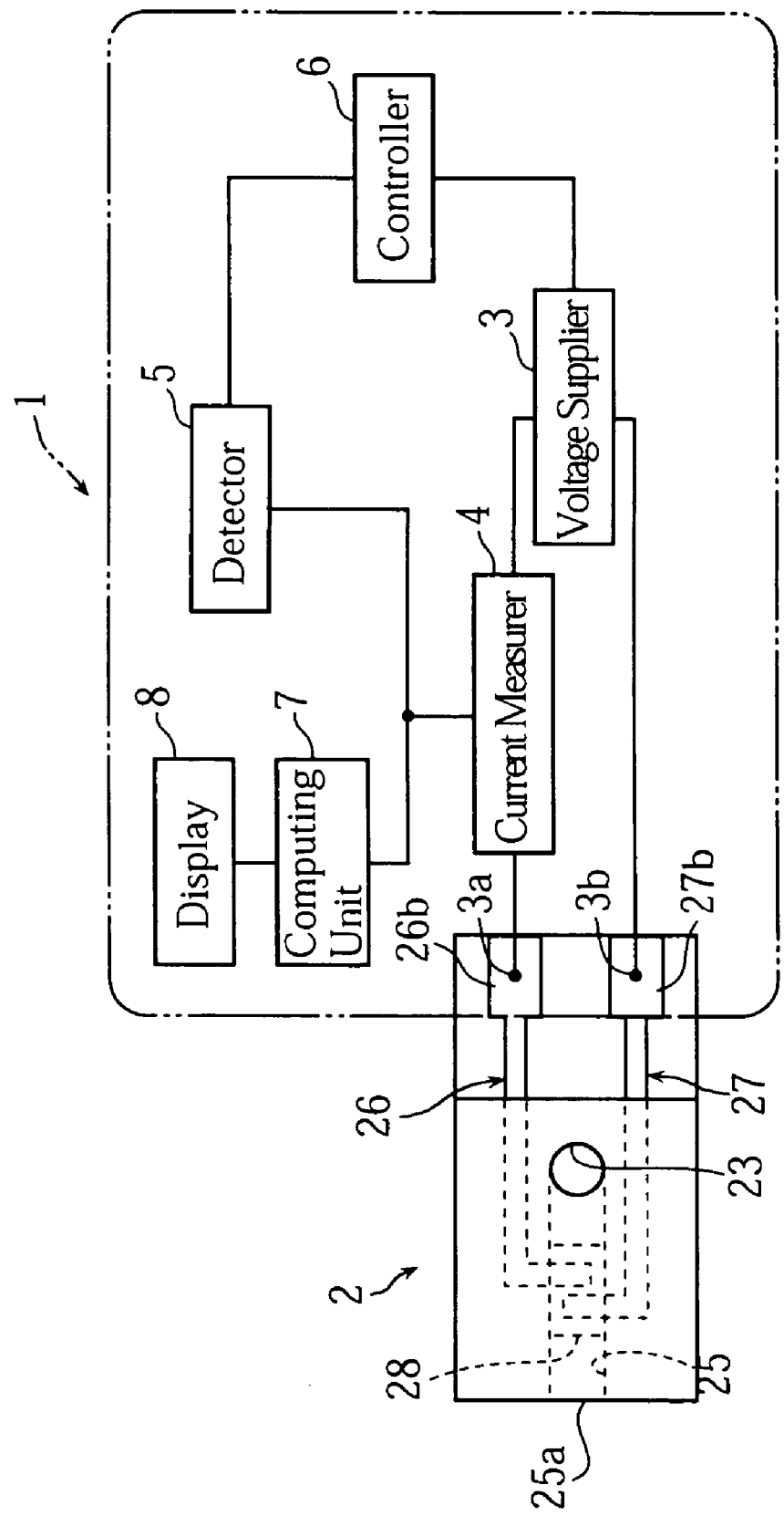
FIG. 1 shows a concentration measuring apparatus to which a glucose sensor according to the present invention is mounted, the concentration measuring apparatus being illustrated in a block diagram, while the glucose sensor being illustrated in a plan view.

FIG. 1 shows a concentration measuring apparatus 1 for measuring the glucose level of a sample liquid such as blood containing glucose by using a glucose sensor 2 according to the present invention. The concentration measuring apparatus 1 generally comprises a voltage supplier 3, a current measurer 4, a detector 5, a controller 6, a computing unit 7 and a display 8.

Figure 2:
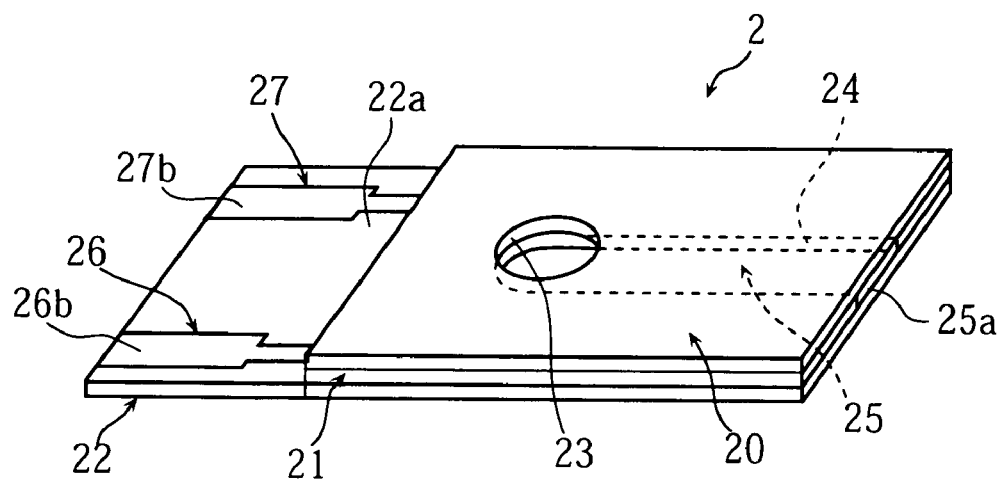
FIG. 2 is an entire perspective view showing an example of glucose sensor.
Figure 3:
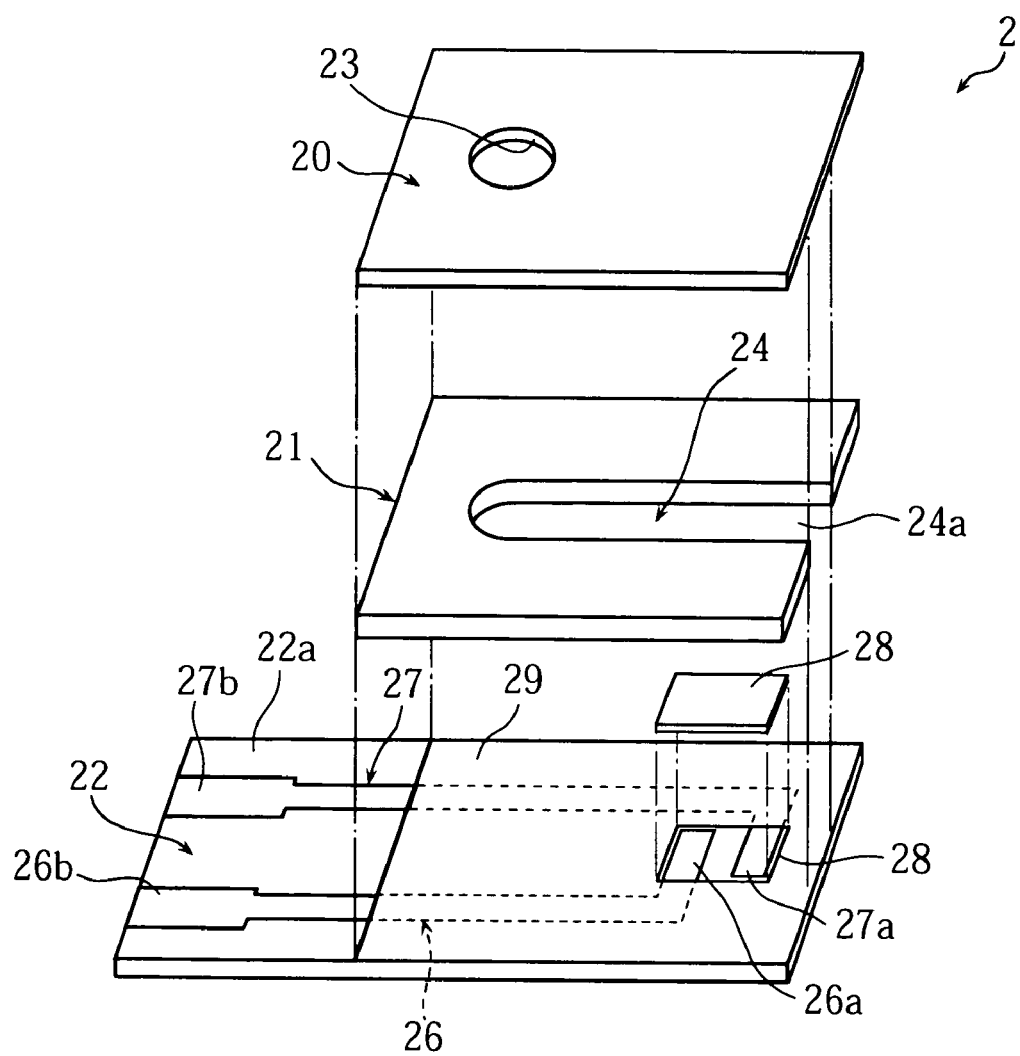
FIG. 3 is an exploded perspective view showing the glucose sensor of FIG. 2.

As shown in FIGS. 2 and 3, the glucose sensor 2, which is disposable, includes a cover plate 20, a spacer 21 and a substrate 22.

The cover plate 20 is formed with a hole 23, whereas the spacer 21 is formed with a narrow slit 24 communicating with the hole 23 and having an open front end 24a. With the cover plate 20 and the spacer 21 stacked on the upper surface 22a of the substrate 22, the slit 24 defines a capillary 25. The capillary 25 has a volume of 0.1 to 0.5 μL, for example, and communicates with the outside through the front end opening 24a of the slit 24 and the hole 23. The front end opening 24a provides a sample introduction port 25a. The sample liquid supplied through the sample introduction port 25a travels through the capillary 25 toward the hole 23 by capillary action.

The upper surface 22a of the substrate 22 is formed with a first electrode 26, a second electrode 27 and a reagent layer 28.

The first and the second electrodes 26 and 27 mostly extend longitudinally of the substrate 22 and respectively have ends 26a and 27a extending widthwise of the substrate 22. The upper surface 22a of the substrate 22 is covered by an insulating film 29, with the ends 26a, 26b, 27a and 27b of the first and the second electrodes 26 and 27 exposed.

The reagent layer 28, which is in a solid state, for example, is provided to bridge between the ends 26a and 27a of the first and the second electrodes 26 and 27. The reagent layer 28 may include a relatively large amount of Ru compound (electron carrier) in the oxidized form and a relatively small amount of GDH (glucose dehydrogenase). For example, the content of GDH in the reagent layer may be set to an amount which corresponds to glucose dehydrogenase activity of 1.0 to 10.0 U, whereas the content of the Ru compound in the reagent layer may be set so that the Ru compound in the sample liquid filling the capillary 25 has a concentration of 1.0 to 5.0 wt %.

As the Ru compound in the oxidized form, any Ru compound can be used as long as it serves as an electron carrier. Preferably, a Ru complex represented by the chemical formula given below may be used.

Examples of X in the above formula include $NH_3$, halogen ion, CN, pyridine, nicotinamide and $H_2O$. Preferably, a Ru complex in which X is $NH_3$ or halogen ion is used. In the above formula, n+ represents the valency of the Ru complex, which is determined by the kind of X.

In the reagent layer 28, the proportion of the Ru compound is made larger than GDH, so that the influence of the RU compound on the solubility of the reagent layer 28 is large. The Ru complex as a Ru compound represented by the above formula is unlikely to be crystallized, is capable of keeping the state of minute particles, and has a high solubility. Therefore, the reagent layer 28 as a whole has a high solubility and is easily dissolved by the supply of blood. Therefore, in the glucose sensor 2, even when the volume of the capillary 25 is set to be small like the above-described range, a reaction system in a generally uniform liquid phase can be properly established in the capillary 25.

As the GDH, it is preferable to use one consisting of a subunit having glucose dehydrogenase activity, and cytochrome c as an electron carrying protein combined to the subunit. Preferably, as the subunit having glucose dehydrogenase activity and cytochrome c, use may be made of ones derived from microorganisms belonging to e.g. the *burkholderia* genus, and specifically ones derived from *burkholderia* cepacia strain KS1, for example. However, the subunit having glucose dehydrogenase activity and cytochrome c are not limited to ones derived from microorganisms belonging to the *burkholderia* genus. For example, as long as the intended function can be achieved, use may be made of ones derived from other microorganisms or living cells or ones provided by obtaining the expression code of the aimed subunit from a microorganism belonging to the *burkholderia* genus and transferring the vector including the expression code to a host for causing the production from the host.

When the strain KS1 belonging to the *burkholderia* genus is used as the microorganism, the subunit having glucose dehydrogenase activity is obtained as an α subunit having a molecular weight of about 60 kDa, whereas cytochrome C is obtained as a β subunit having a molecular weight of about 43 kDa. In the strain KS1, GDH is produced in which a γ subunit having a molecular weight of about 14 kDa is attached to the α subunit and the β subunit. It should be noted that the molecular weight is measured in SDS-polyacrylamide gel electrophoresis under the reduced condition. In this case, from the viewpoint of increasing the reaction rate with glucose, it is preferable to use αGDH in which the γ subunit is attached to the α subunit. On the other hand, from the viewpoint of improving the electron carriage speed, it is preferable to use CyGDH in which the β subunit (cytochrome C) is attached to αGDH.

The voltage supplier 3 shown in FIG. 1 serves to apply a constant voltage across the end 26b of the first electrode 26 and the end 27b of the second electrode 27. By mounting the glucose sensor 2 at a mount portion (not shown) provided in the glucose concentration measuring apparatus 1, the voltage supplier 3 is electrically connected to the ends 26b, 27b of the glucose sensor 2 via a first and a second contactors 3a and 3b. As the voltage supplier 3, use may be made of a DC power source such as a dry cell or rechargeable battery.

The current measurer 4 serves to measure the responsive current, which corresponds to e.g. the amount of electrons emitted from the Ru compound in the reduced form when a voltage is applied to the reaction system.

The detector 5 serves to check whether or not the sample liquid is supplied to the reagent layer 28 and the glucose level measurement is ready after the glucose sensor 2 is mounted to the glucose level measuring apparatus 1.

The controller 6 controls the voltage supplier 3 to select between a state in which a voltage is applied across the first and the second electrodes 26 and 27 (closed circuit) and a state in which no voltage is applied (open circuit).

The computing unit 7 serves to compute the glucose level in the sample liquid based on the responsive current measured by the current measurer 4.

Each of the detector 5, the controller 6 and the computing unit 7 may comprise a CPU and a memory such as a ROM or a RAM, for example. However, the entirety of the detector 5, the controller 6 and the computing unit 7 may be provided by connecting a plurality of memories to a single CPU. The results of computation by the computing unit 7 are displayed at the display 8. The display 8 may comprise an LCD, for example.

Figure 4:
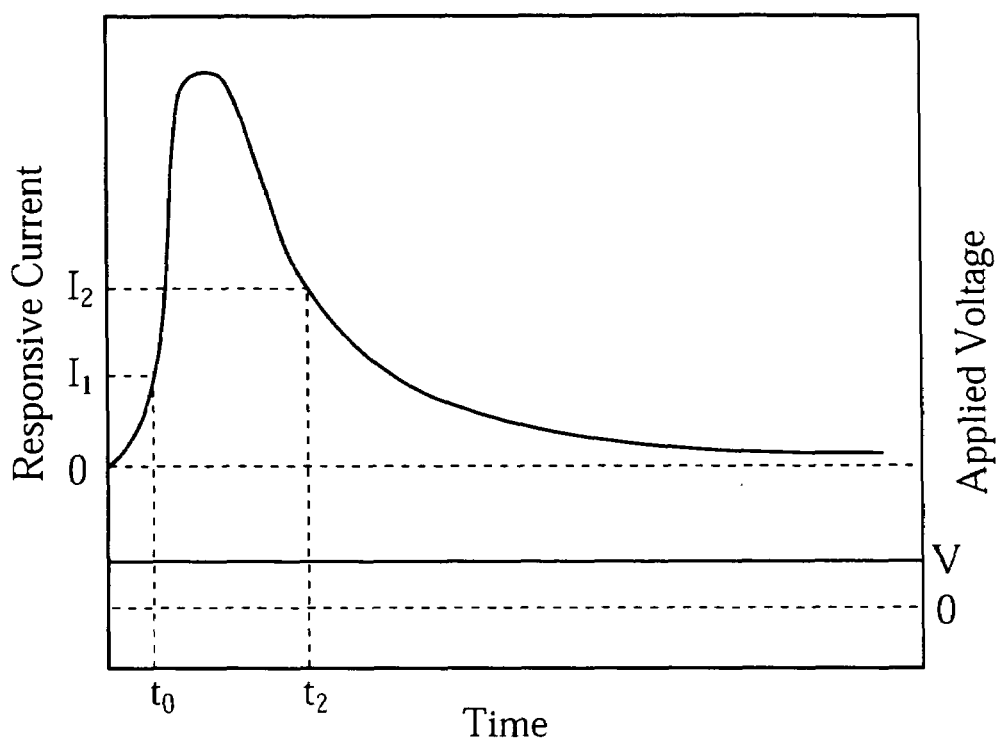
FIG. 4 is a graph showing an example of change with time in the voltage applied across the first and the second electrodes and in the responsive current in the glucose level measurement.

Next, the process of the measurement of the glucose level in a sample liquid will be described with reference to FIGS. 4 and 5 in addition to FIGS. 1 through 3.

First, as shown in FIG. 1, the glucose sensor 2 is set to the glucose concentration measuring apparatus 1. As a result, the end 26b of the first electrode 26 of the glucose sensor 2 comes into contact with the first contactor 3a of the concentration measuring apparatus 1, whereas the end 27b of the second electrode 27 comes into contact with the second contactor 3b. In this state, the first and the second electrodes 26 and 27 are electrically connected to the voltage supplier 3, as noted before. In the actual measurement, before the sample liquid is supplied to the glucose sensor 2, the voltage supplier 3 applies a constant voltage across the first and the second electrodes 26 and 27 under the control by the controller 6. For example, the voltage to be applied is set to a range of 100 to 500 mV.

Subsequently, a sample liquid such as blood is supplied through the sample introduction port 25a of the glucose sensor 2. The sample liquid travels through the capillary 25 of the glucose sensor 2 by capillary action. In this process, the sample liquid dissolves the reagent layer 28 to establish a reaction system in a liquid phase. In the reaction system, glucose is oxidized by GDH, whereas the Ru compound is changed to the reduced form.

When a constant voltage is applied across the first and the second electrodes 26 and 27 through the two ends 26b and 27b, the Ru compound in the reduced form existing in the reagent layer 28 moves to the end 26a side of the first electrode 26 and emits electrons to the end 26a to become the Ru compound in the oxidized form. Therefore, with the constant voltage applied across the first and the second electrodes 26 and 27 by the voltage supplier 3, the amount of electrons supplied by the Ru compound in the reduced form is measured by the current measurer 4 via the first electrode 26 and the first contactor 3a as the responsive current.

The responsive current measured by the current measurer 4 is monitored by the detector 5. As shown in FIG. 4, at the time point $t_0$ when the responsive current exceeds a threshold $I_1$ (e.g. 0.1 to 3.0 μA), the detector 5 detects that the sample liquid has been supplied to the reagent layer 28 and the reagent layer 28 has dissolved.

When the supply of the sample liquid is detected by the detector 5, the current measurer 4 measures the responsive current for computation $I_2$ at the time point $t_2$ when a predetermined time period (e.g. $t_2$-$t_0$ is no more than ten seconds, preferably no more than five seconds) has elapsed from the detection.

Figure 5:
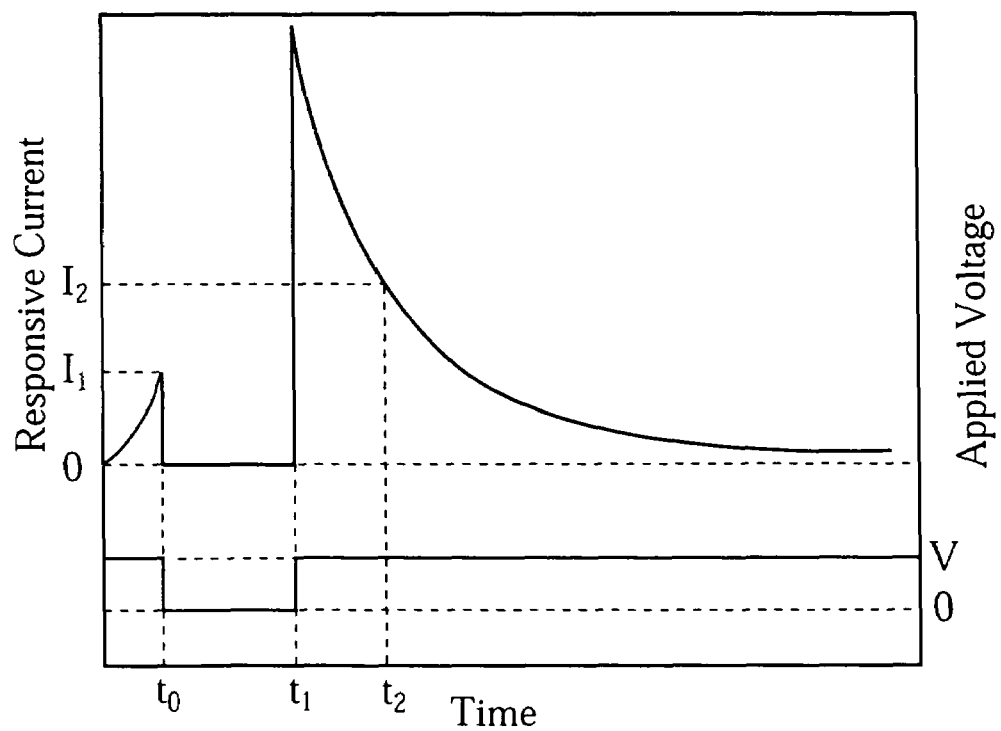
FIG. 5 is a graph showing another example of change with time in the voltage applied across the first and the second electrodes and in the responsive current in the glucose level measurement.

Alternatively, as shown in FIG. 5, after the supply of the sample liquid is detected by the detector 5, the voltage application may be interrupted for a certain time period until the time point $t_1$ (e.g. $t_1$-$t_0$ is no more than ten seconds, preferably no more than three seconds). In this case, the voltage application is restarted from the time point $t_1$, and the responsive current at the time point $t_2$ when a predetermined time period (e.g. $t_2-t_1$ is no less than three seconds, preferably no more than three to five seconds) has elapsed from the restart of the voltage application is utilized as the responsive current for computation $I_2$.

The computing unit 7 computes the glucose level in the sample liquid based on the responsive current for computation $I_2$. The glucose level is computed by converting the responsive current to a voltage value and then applying the voltage value to the calibration curve which is prepared in advance for showing the relationship between voltage values and glucose levels. For example, the calibration curve may be stored, as data, in a ROM along with the program for executing the computation.

In this embodiment, the reagent layer 28 is provided by a combination of a Ru compound and a particular GDH (such as αGDH or CyGDH). In such a reagent layer 28, the reaction rate (including both the enzyme reaction rate and the electron carriage speed (Vmax/Km)) when the sample liquid is supplied is large. For example, in the case of CyGDH, Vmax/Km is about 2100 mM. Therefore, glucose reaction proceeds at the maximum rate even when the glucose level is low, so that the amount of reaction product produced per unit time becomes constant regardless of the glucose level. Further, the reaction with glucose can be completed in less than one second even when the glucose level is about 1000 mg/dL, and a large amount of reaction product can be obtained even from a small amount of analyte. Therefore, the end point can be reached in a relatively short period of time regardless of the glucose level. As a result, as will become clear from Examples which will be described later, the measurement time ($t_2-t_0$ in FIGS. 4 and 5) can be set short while reducing the amount of the sample liquid (e.g. blood) as a measurement object. Moreover, even in analyzing a small amount of analyte having a high glucose level, variation in the responsive current is small when the same glucose level is measured a plurality of times. Thus, a wide measurement range can be covered.

As noted above, the reagent layer 28 has a high solubility. Therefore, even when the capillary is made small for analyzing a small amount of sample, a reaction system in a generally uniform liquid phase can be established in the capillary 25 when the sample liquid is supplied. Thus, even when blood (analyte) is used as the sample liquid, the responsive current can be measured with high reproducibility without being largely influenced by the blood cell components.

Since a Ru compound such as a Ru complex is stable in the oxidized form, it is unlikely to change to the reduced form. Therefore, the biosensor utilizing a Ru compound has a high storage stability and low background. Therefore, the measurement accuracy is not deteriorated even when the glucose level of a sample is low or when a small amount of sample is used.

In this embodiment, the method of measuring a glucose level by a combination of a glucose sensor and a concentration measuring apparatus has been described. However, the glucose level measuring method according to the present invention can be realized also by using a meter provided with an immobilized-enzyme electrode.

EXAMPLE

Hereinafter, it is demonstrated that, in the measurement of a glucose level by utilizing enzyme reaction, a glucose sensor having a reagent layer provided by the combination of a Ru complex and αGDH or βGDH exhibits a high reaction rate (short measurement time), covers a wide measurement range, has a high reproducibility, and is less likely to be influenced by the hematocrit (Ht), even when a minute amount of analyte is used.

[Preparation of Glucose Sensor]

As the glucose sensor, use was made of one including a substrate on which a first electrode, a second electrode, a reagent layer and a capillary are formed (See FIGS. 2 and 3). The first and the second electrodes were formed by applying carbon ink onto the substrate by screen printing and then drying the ink. The volume of the capillary was basically set to 0.3 μL. However, as will be described later, in checking the influence of Hct, capillaries having a volume of 0.4 μL and 0.5 μL were also utilized. The reagent layer was made to have a two-layer structure comprising an electron carriage layer and an enzyme containing layer. The electron carriage layer was formed by applying 0.4 μL of first liquid material containing electron carrier onto the substrate and then drying the first liquid material by blowing (30° C., 10% Rh). The enzyme containing layer was formed by applying 0.3 μL of second liquid material containing oxidoreductase onto the electron carriage layer and then drying the second liquid material by blowing (30° C., 10% Rh).

The first liquid material was prepared by mixing the ingredients (1), (2), (3), (4) shown in Table 1 below in the mentioned order, leaving the liquid mixture for one to three days, and then adding an electron carrier to the liquid mixture. The second liquid material was prepared by dissolving oxidoreductase in 0.1% CHAPS.

As the electron carrier, use was made of $[Ru(NH_3)_6]Cl_3$ (available from ALDRICH) which will be hereinafter simply referred to as "Ru" or "Ru complex", or $K_3[Fe(III)(CN)_6]$ ("28637-75" available from NACALAI TESQUE, INC.) which will be hereinafter simply referred to as "Ferri". As the oxidoreductase, use was made of CyGDH, αGDH or PQQGDH. As noted above, CyGDH consists of an α subunit, a β subunit and a γ subunit, whereas αGDH consists of an α subunit and a γ subunit. As for PQQGDH, PQQ (pyrroloquinoline quinone) serves as the coenzyme.

TABLE 1

| First Liquid Material Composition (excluding electron carrier) | | | | | | |
|---|---|---|---|---|---|---|
| (1) SWN Solution | | (2) CHAPS Solution | | (3) Distilled | (4) ACES Solution | |
| Conc. | Vol. | Conc. | Vol. | Water | Conc. | Vol. |
| 1.2% | 250 μL | 10% | 25 μL | 225 μL | 200 mM | 500 μL |

In Table 1 and the others ones, SWN is an abbreviation of Lucentite SWN, CHAPS is an abbreviation of 3-[(3-cholamidopropyl)dimethylammonio]propanesulfonic acid, and ACES is an abbreviation of N-(2-acetamido)-2-aminoetanesulfonic acid. As the SWN, use was made of "3150" available from CO-OP Chemical Kabushiki Kaisha. As the CHAPS, use was made of "KC062" available from DOJINDO LABORATORIES. As the ACES, use was made of "ED067" available from DOJINDO LABORATORIES. The ACES solution was adjusted to pH 7.5.

[Preparation of Glucose Solution]

As the glucose solution, use was made of whole blood (analyte) whose glucose level and Hct had been adjusted to intended values. Specifically, Hct was adjusted to 42% unless any particular limitation exists. The glucose level was adjusted to 0, 101, 412, 624, 820 or 1034 mg/dL in accordance of the purpose of the test.

[Measurement of Responsive Current]

With a constant voltage (200 mV) applied across the first and the second electrodes of the glucose sensor, the analyte in an amount corresponding to the capillary volume (0.3 µL, 0.4 µL, 0.5 µL) was supplied to the reagent layer, and the responsive current was measured after a predetermined time period (five or ten seconds) had elapsed from the analyte supply.

[Evaluation of Measurement Range]

Responsive current was measured by using analytes of different glucose levels, and the measurement range was evaluated based on the linearity of plot points obtained with the glucose level taken on the abscissa while the responsive current taken on the ordinate. The measurements of responsive current after five seconds from the analyte supply are shown in FIGS. 6A-6D and 7A-7D, whereas the measurements of responsive current after ten minutes from the analyte supply are shown in FIGS. 8A-8D and 9A-9D. Each of the plot points indicates the average of responsive current values of ten glucose sensors having the same composition. The evaluation was performed with respect to plural kinds of glucose sensors each containing oxidoreductase and electron carrier as given in Table 2 below. The sensors indicated as A-1 to 3 and B-1 to 3 in Table 2 are the glucose sensors of the present invention, whereas others are glucose sensors for comparison. In Table 2, the activity of oxidoreductase is the activity in a liquid phase reaction system established when the analyte is supplied to the capillary, whereas the content of electron carrier indicates the weight percent of the electron carrier in the liquid phase reaction system.

TABLE 2

Sensor Composition

| Sensor No. | Oxidoreductase Kind | Activity(U) | Electron Carrier Kind | Content (wt %) |
|---|---|---|---|---|
| A-1 or 2 or 3 | CyGDH | 2 | Ru | 2 or 4 or 8 |
| B-1 or 2 or 3 | αGDH | 2 | Ru | 2 or 4 or 8 |
| C-1 or 2 or 3 | PQQGDH | 2 | Ru | 2 or 4 or 8 |
| D-1 or 2 or 3 | PQQGDH | 20 | Ru | 2 or 4 or 8 |
| E-1 or 2 or 3 | CyGDH | 2 | Ferri | 2 or 4 or 8 |
| F-1 or 2 or 3 | αGDH | 2 | Ferri | 2 or 4 or 8 |
| G-1 or 2 or 3 | PQQGDH | 2 | Ferri | 2 or 4 or 8 |
| H-1 or 2 or 3 | PQQGDH | 20 | Ferri | 2 or 4 or 8 |

[Evaluation of Reproducibility]

The reproducibility was evaluated based on variations of measurements obtained under the same condition (variations of measurements when the composition of the glucose sensors and the glucose level of the analytes are the same). The variations were evaluated by coefficients of variation (C.V.). Each C.V. was computed based on ten pieces of measurement data used as the basis for computing the plot points in FIGS. 6 through 9. The results with respect to the values five seconds after are given in Tables 3 through 5, whereas the results with respect to the values ten seconds after are given in Tables 6 through 8.

TABLE 3

[Reproducibility] C.V. (%):
(Electron carrier 8 wt %, Responsive current five-second value)

| Sensor No. | Composition of Reagent layer | Glucose level (mg/dL) | | | | | |
|---|---|---|---|---|---|---|---|
| | | 0 | 101 | 412 | 624 | 820 | 1034 |
| A-3 | Ru8%-Cy2U | 6.7 | 1.2 | 1.4 | 3.6 | 0.7 | 3.5 |
| B-3 | Ru8%-α2U | 9.4 | 3.5 | 1.5 | 1.3 | 2.5 | 1.8 |
| C-3 | Ru8%-PQQ2U | 6.1 | 11.1 | 11.9 | 13.2 | 8.0 | 8.8 |
| D-3 | Ru8%-PQQ20U | 18.1 | 2.1 | 0.9 | 5.0 | 13.8 | 7.6 |
| E-3 | Ferri8%-Cy2U | 5.0 | 6.7 | 4.4 | 2.1 | 5.3 | 2.3 |
| F-3 | Ferri8%-α2U | 11.1 | 5.7 | 4.3 | 3.3 | 7.1 | 3.6 |
| G-3 | Ferri8%-PQQ2U | 6.0 | 3.0 | 7.7 | 10.6 | 3.7 | 9.6 |
| H-3 | Ferri8%-PQQ20U | 12.9 | 7.2 | 2.3 | 1.9 | 1.3 | 2.9 |

TABLE 4

[Reproducibility] C.V. (%):
(Electron carrier 4 wt %, Responsive current five-second value)

| Sensor No. | Composition of Reagent layer | Glucose level (mg/dL) | | | | | |
|---|---|---|---|---|---|---|---|
| | | 0 | 101 | 412 | 624 | 820 | 1034 |
| A-2 | Ru4%-Cy2U | 8.9 | 2.2 | 1.0 | 1.9 | 2.9 | 3.8 |
| B-2 | Ru4%-α2U | 8.9 | 1.5 | 3.1 | 2.3 | 2.4 | 6.8 |
| C-2 | Ru4%-PQQ2U | 12.4 | 9.2 | 5.3 | 14.5 | 23.1 | 11.2 |
| D-2 | Ru4%-PQQ20U | 10.5 | 1.4 | 2.8 | 5.1 | 6.0 | 6.1 |
| E-2 | Ferri4%-Cy2U | 11.0 | 2.9 | 1.8 | 2.2 | 1.6 | 2.7 |
| F-2 | Ferri4%-α2U | 11.0 | 10.5 | 5.4 | 6.0 | 28.0 | 6.3 |
| G-2 | Ferri4%-PQQ2U | 6.5 | 6.0 | 12.5 | 4.4 | 8.2 | 3.9 |
| H-2 | Ferri4%-PQQ20U | 4.9 | 8.0 | 5.8 | 5.4 | 9.5 | 22.9 |

TABLE 5

[Reproducibility] C.V. (%):
(Electron carrier 2 wt %, Responsive current five-second value)

| Sensor No. | Composition of Reagent layer | Glucose level (mg/dL) | | | | | |
|---|---|---|---|---|---|---|---|
| | | 0 | 101 | 412 | 624 | 820 | 1034 |
| A-1 | Ru2%-Cy2U | 17.2 | 2.0 | 1.0 | 1.0 | 2.2 | 3.7 |
| B-1 | Ru2%-α2U | 22.4 | 1.6 | 1.8 | 9.3 | 7.1 | 13.0 |
| C-1 | Ru2%-PQQ2U | 11.1 | 7.6 | 23.5 | 15.8 | 8.1 | 32.1 |
| D-1 | Ru2%-PQQ20U | 8.6 | 1.8 | 2.2 | 6.1 | 9.0 | 4.7 |
| E-1 | Ferri2%-Cy2U | 10.4 | 2.3 | 2.0 | 22.8 | 37.6 | 39.1 |
| F-1 | Ferri2%-α2U | 15.8 | 4.7 | 33.8 | 36.0 | 41.4 | 16.6 |
| G-1 | Ferri2%-PQQ2U | 5.0 | 6.9 | 5.3 | 10.2 | 12.7 | 6.9 |
| H-1 | Ferri2%-PQQ20U | 6.5 | 6.4 | 11.9 | 8.7 | 39.2 | 28.4 |

TABLE 6

[Reproducibility] C.V. (%):
(Electron carrier 8 wt %, Responsive current ten-second value)

| Sensor No. | Composition of Reagent layer | Glucose level (mg/dL) | | | | | |
|---|---|---|---|---|---|---|---|
| | | 0 | 101 | 412 | 624 | 820 | 1034 |
| A-3 | Ru8%-Cy2U | 6.4 | 2.2 | 5.1 | 4.4 | 3.0 | 2.6 |
| B-3 | Ru8%-α2U | 10.0 | 3.2 | 2.9 | 3.7 | 3.5 | 3.3 |
| C-3 | Ru8%-PQQ2U | 6.9 | 7.5 | 9.4 | 12.4 | 6.8 | 10.6 |
| D-3 | Ru8%-PQQ20U | 16.0 | 4.0 | 2.0 | 2.5 | 7.2 | 3.4 |
| E-3 | Ferri8%-Cy2U | 4.2 | 5.9 | 4.5 | 3.8 | 5.7 | 3.1 |
| F-3 | Ferri8%-α2U | 7.4 | 6.1 | 6.3 | 2.4 | 7.5 | 4.6 |
| G-3 | Ferri8%-PQQ2U | 4.5 | 2.4 | 6.2 | 10.5 | 3.5 | 9.5 |
| H-3 | Ferri8%-PQQ20U | 9.7 | 6.5 | 1.4 | 1.9 | 2.5 | 3.3 |

TABLE 7

[Reproducibility] C.V. (%):
(Electron carrier 4 wt %, Responsive current ten-second value)

| Sensor No. | Composition of Reagent layer | Glucose level (mg/dL) | | | | | |
|---|---|---|---|---|---|---|---|
| | | 0 | 101 | 412 | 624 | 820 | 1034 |
| A-2 | Ru4%-Cy2U | 10.6 | 2.0 | 2.6 | 2.1 | 2.1 | 2.1 |
| B-2 | Ru4%-α2U | 10.4 | 1.5 | 3.4 | 2.4 | 3.0 | 3.2 |
| C-2 | Ru4%-PQQ2U | 13.5 | 5.2 | 5.1 | 14.5 | 21.8 | 10.7 |
| D-2 | Ru4%-PQQ20U | 10.4 | 2.6 | 2.8 | 2.6 | 5.4 | 4.5 |
| E-2 | Ferri4%-Cy2U | 7.0 | 2.9 | 2.9 | 2.1 | 2.0 | 2.2 |
| F-2 | Ferri4%-α2U | 6.6 | 5.5 | 5.1 | 6.1 | 35.8 | 21.0 |
| G-2 | Ferri4%-PQQ2U | 4.1 | 3.7 | 9.8 | 3.7 | 7.7 | 4.7 |
| H-2 | Ferri4%-PQQ20U | 2.8 | 3.6 | 2.1 | 5.1 | 4.9 | 31.2 |

TABLE 8

[Reproducibility] C.V. (%):
(Electron carrier 2 wt %, Responsive current ten-second value)

| Sensor No. | Composition of Reagent layer | Glucose level (mg/dL) | | | | | |
|---|---|---|---|---|---|---|---|
| | | 0 | 101 | 412 | 624 | 820 | 1034 |
| A-1 | Ru2%-Cy2U | 18.7 | 3.6 | 1.5 | 1.0 | 1.8 | 1.7 |
| B-1 | Ru2%-α2U | 21.4 | 2.2 | 0.9 | 3.2 | 28.0 | 31.8 |
| C-1 | Ru2%-PQQ2U | 13.0 | 7.0 | 22.5 | 16.7 | 8.6 | 30.3 |
| D-1 | Ru2%-PQQ20U | 12.8 | 1.3 | 1.5 | 2.7 | 3.9 | 2.3 |
| E-1 | Ferri2%-Cy2U | 6.9 | 0.9 | 2.0 | 27.8 | 48.3 | 44.6 |
| F-1 | Ferri2%-α2U | 10.5 | 3.2 | 18.8 | 19.1 | 39.9 | 22.9 |
| G-1 | Ferri2%-PQQ2U | 3.8 | 4.2 | 5.4 | 8.7 | 11.9 | 7.8 |
| H-1 | Ferri2%-PQQ20U | 8.4 | 13.3 | 14.6 | 16.5 | 38.5 | 30.6 |

[Examination of influence of Hct in analyte]

To examine the influence of Hct, responsive current after a predetermined time period had elapsed from the analyte supply was measured by using a plurality of analytes having the same glucose level and different Hct values. The measurement was performed with respect to the inventive sensors 1-3 and a comparative sensor by using a plurality of samples for each. The spacer thickness and the capillary volume (analyte amount) of the inventive sensor 1 were set to 58 μm and 0.5 μL, respectively. The spacer thickness and the capillary volume (analyte amount) of the inventive sensor 2 were set to 44 μm and 0.4 μL, respectively. The spacer thickness and the capillary volume (analyte amount) of the inventive sensor 3 were set to 33 μm and 0.3 μL, respectively. The reagent layer of the inventive sensors 1-3 contained about 2.0 U of CyGDH and 4 wt % (as converted to the concentration of the electron carrier) of [Ru(NH$_3$)$_6$]Cl$_3$. As the comparative sensor, use was made of a sensor for use in a blood glucose test meter "Glucocard" available from ARKRAY, INC. In this sensor, GOD is used as the oxidoreductase, and Ferri is used as the electron carrier.

The results when the inventive sensors 1-3 are used are shown in FIGS. 10A-10C, whereas the results when the comparative sensor is used are given in FIG. 10D. In FIGS. 10A-10D, the responsive current obtained when Hct is 42% is set as the reference, and the variations (Bias) relative to the reference are indicated on the ordinate. The abscissa in FIGS. 10A-10C is time, whereas the abscissa in FIG. 10D is Hct. Each of the plot points in each figure indicates an average of five measurements. The plot points in FIG. 10D were computed based on the value after 30 seconds from the analyte supply.

[Consideration of Evaluation Results]

Figure 6B:
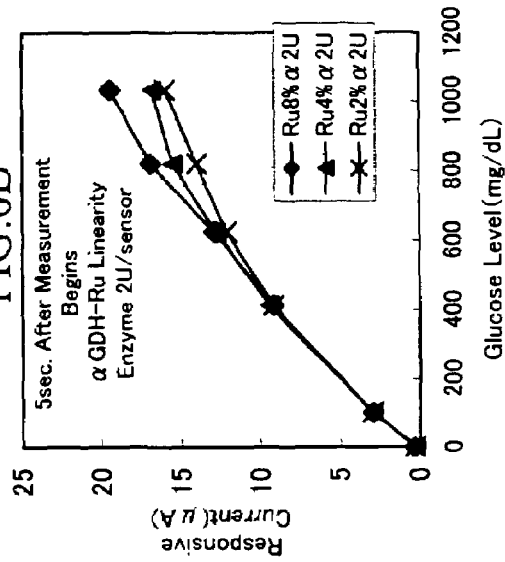
FIGS. 6A-6D each is a graph showing the relationship between the glucose level and the responsive current after five seconds from the start of the reaction when the reagent layer is provided by using a Ru complex.
Figure 6D:
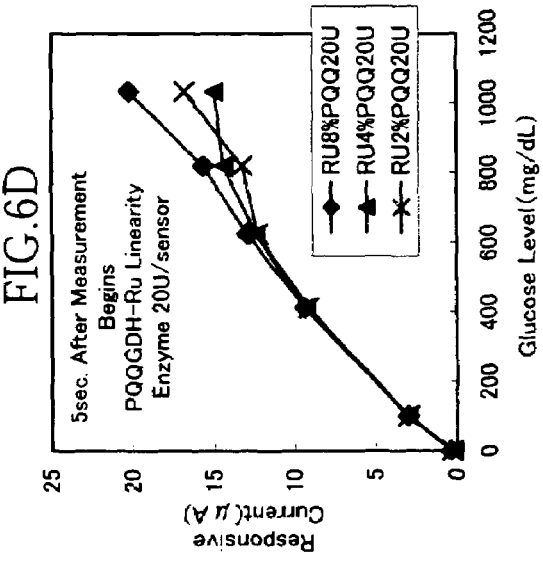
Figure 6A:
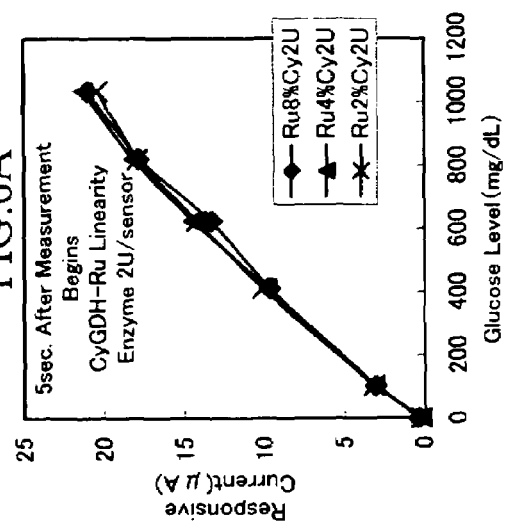
Figure 6C:
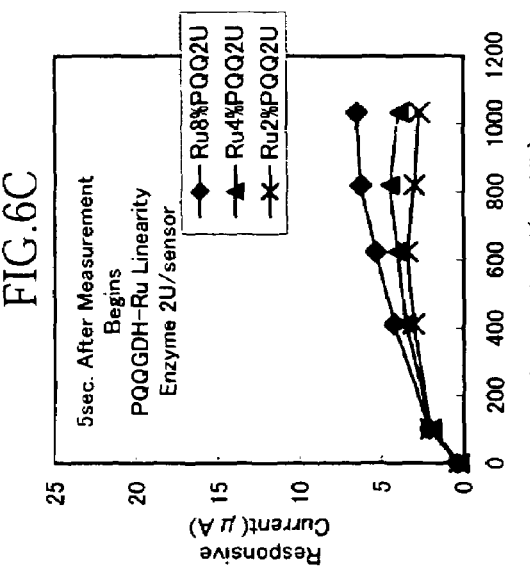
Figure 7A:
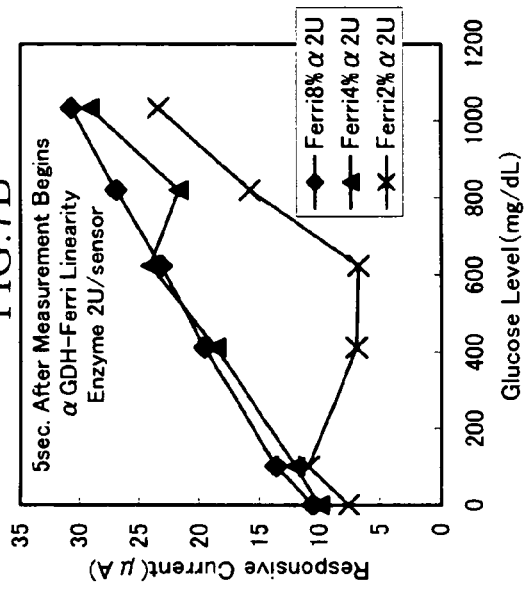
FIGS. 7A-7D each is a graph showing the relationship between the glucose level and the responsive current after five seconds from the start of the reaction when the reagent layer is provided by using an iron complex.
Figure 7B:
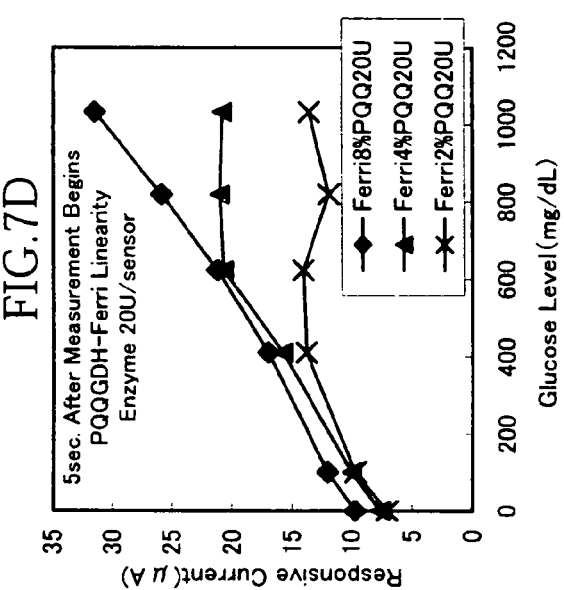
Figure 7C:
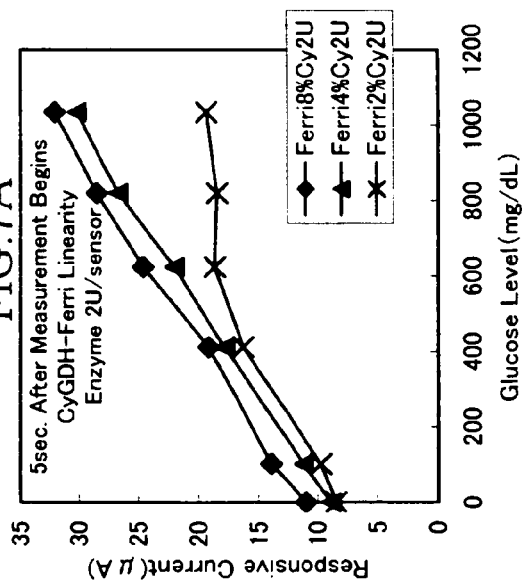
Figure 7D:
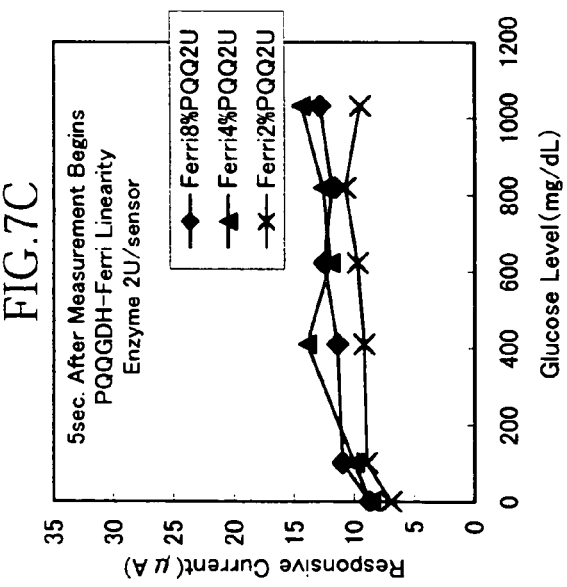
Figure 8A:
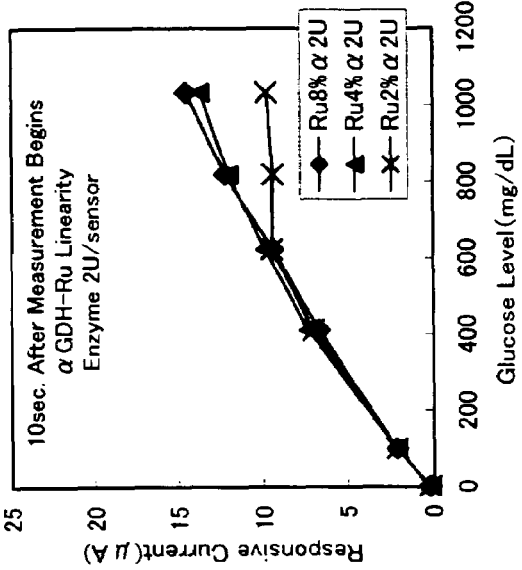
FIGS. 8A-8D each is a graph showing the relationship between the glucose level and the responsive current after ten seconds from the start of the reaction when the reagent layer is provided by using a Ru complex.

As shown in FIGS. 6A and 8A, the glucose sensors (A-1 to 3) containing CyGDH as the enzyme and Ru complex as the electron carrier exhibit high linearity even when the content of the Ru complex is small. Since this result is obtained for both of the values after five seconds and the values after ten seconds, as well as for the high glucose level range (600 to 1000 mg/dL), it can be concluded that the system provided by the combination of CyGDH and Ru complex has a high reaction rate (low Km). As can be understood from Tables 3-8, the system provided by the combination of CyGDH and Ru complex exhibits a low C.V. and an excellent reproducibility. Summarizing the above results, it can be concluded that, in the system provided by the combination of CyGDH and Ru complex, the linearity and reproducibility in both of the values after five seconds and the values after ten seconds do not change greatly even when the concentration of Ru changes, and the reaction can be sufficiently completed in five seconds for enabling the determination of the glucose level.

Figure 8B:
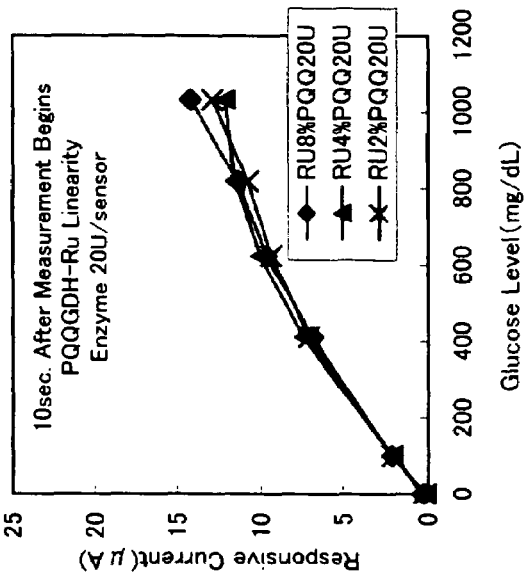
Figure 8C:
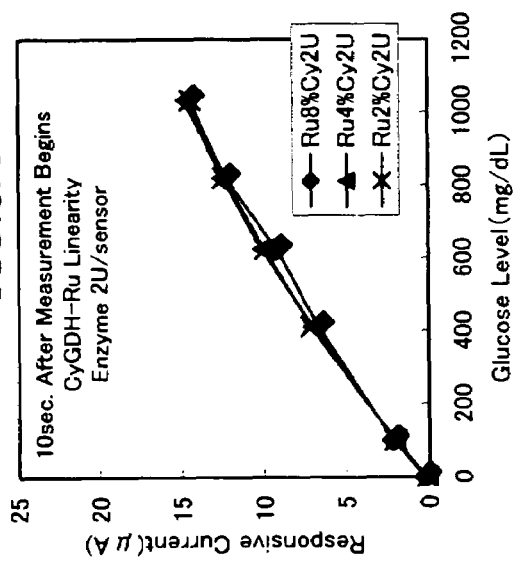
Figure 8D:
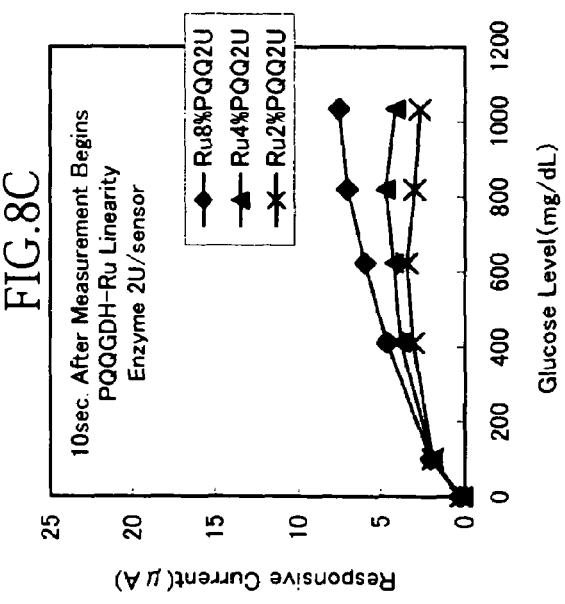

As shown in FIGS. 6B and 8B, in the glucose sensors (B-1 to B-3) containing αGDH and Ru complex, the results obtained when the content of Ru complex is set low (2 wt %) are similar to those of the system provided by the combination of CyGDH and Ru complex, although the linearity is slightly deteriorated in the high glucose concentration range (600 to 1000 mg/dL). Therefore, also with respect to the system provided by the combination of αGDH and Ru complex, it can be concluded that the reaction rate is high. Further, as can be understood from Tables 3-8, the system basically has a high reproducibility. Therefore, in the system provided by the combination of αGDH and Ru complex again, the reaction can be sufficiently completed in five seconds for enabling the determination of the glucose level.

On the other hand, as can be understood FIGS. 6C, 6D and FIGS. 8C, 8D, in the glucose sensors (C-1 to 3 and D-1 to 3) provided by the combination of Ru and PQQGDH, the content of Ru complex and oxidoreductase need be increased to assure the linearity. In this case, however, the total amount of the reagent layer increases, which does not conform to the policy to reduce the capillary size to enable the analysis of a small amount of analyte (0.3 μL), and hence, is not practical.

As shown in FIGS. 7A-7D and 9A-9D, the glucose sensors (E-1 to 3, F-1 to 3, G-1 to 3 and H-1 to 3) using Ferri as the electron carrier has a poor linearity. Further, as can be understood from FIGS. 7C, 7D and FIGS. 9C, 9D, the glucose sensors G-1 to 3 and H-1 to 3 which use PQQGDH as the oxidoreductase are not practical, because the reaction rate, even with a larger amount (20 U) of enzyme, falls short of that of the system provided by the combination of Ru and CyGDH. Moreover, as can be understood from Tables 3-8, these sensors are not practical also in view of the entirely poor reproducibility, which may be caused by the poor solubility of Ferri itself.

As shown in FIGS. 10A-10C, in the inventive sensors 1-3, the influence of Hct decreases as the measurement time increases, and the influence of Hct becomes negligible after ten seconds from the start of the analyte supply. Further, among the inventive sensors, the sensor with a smaller capillary volume and a smaller spacer thickness suffers less influence of Hct. Therefore, to decrease the influence of Hct, it is effective to reduce the thickness of the spacer to cause glucose reaction to occur quickly at the electrode surface of the sensor.

On the other hand, in the comparative sensor, when Hct is high, the influence of Hct is large even after 30 seconds from the start of the analyte supply, and the bias value is close to the value of the inventive sensors after five seconds from the analyte supply. Thus, the inventive sensors 1-3 provided by the combination of Ru complex and CyGDH can perform measurement in a short period of time even with a small amount of analyte and are less likely to be influenced by Hct. In this way, by the combination of Ru complex and CyGDH, a glucose sensor can be provided which is capable of reducing the necessary amount of analyte and the measurement time and which is less likely to be influenced by Hct.

From the above, to measure the glucose level in a short period of time by using a small amount of analyte (e.g. 0.3 μL), the combination of Ru and CyGDH is advantageous in terms of the measurement range, reproducibility, measurement time, and the capability of avoiding the influence of Hct.

Thus, according to the present invention, a small amount of glucose solution of a wide measurement range can be accurately analyzed in a short period of time without large influence of Hct by establishing a reaction system provided by the combination of Ru complex and a particular glucose dehydrogenase (in which cytochrome c is combined or which is derived from a microorganism belonging to the *burkholderia* genus).

The invention claimed is:

1. A glucose level measuring method using glucose dehydrogenase for measuring a glucose level by utilizing a reaction system containing glucose, an enzyme and an electron carrier, wherein the enzyme is glucose dehydrogenase to which cytochrome C is attached and which is separate from the electron carrier; and wherein the electron carrier is a Ru compound represented by a chemical formula as follows:

$Ru(NH_3)_5X]^{n+}$ where X represents $NH_3$, halogen ion, CN, pyridine, nicotinamide or $H_2O$, and n+ represents a valency of the Ru complex, which is determined by the kind of X, the method comprising:

allowing the cytochrome C attached glucose dehydrogenase to oxidize the glucose while reducing the Ru compound;

applying a voltage to the reaction system for the Ru compound to release electrons; and detecting the electrons released by the Ru compound as a response current.

2. The glucose level measuring method according to claim 1, wherein the cytochrome C is derived from a microorganism belonging to a *burkholderia* genus.

3. The glucose level measuring method according to claim 1, wherein the cytochrome C has a molecular weight of about 43 kDa in SDS-polyacrylamide gel electrophoresis under a reduced condition.

4. The glucose level measuring method according to claim 1, wherein the glucose dehydrogenase includes an α subunit having a glucose dehydrogenase activity and a molecular weight of about 60 kDa in SDS-polyacrylamide gel electrophoresis under a reduced condition.

5. The glucose level measuring method according to claim 1, wherein the glucose dehydrogenase includes a γ subunit having a molecular weight of about 14 kDa in SDS-polyacrylamide gel electrophoresis under a reduced condition.

* * * * *